(12) United States Patent
Miller

(10) Patent No.: US 9,022,763 B2
(45) Date of Patent: May 5, 2015

(54) PRESS FURNACE FOR A DENTURE OR PARTIAL DENTURE

(75) Inventor: Stephan Miller, Traunstein (DE)

(73) Assignee: Dekema Dental-Keramikofen GmbH, Freilassing (DE)

( * ) Notice: Subject to any disclaimer, the term of this patent is extended or adjusted under 35 U.S.C. 154(b) by 0 days.

(21) Appl. No.: 13/992,668

(22) PCT Filed: Dec. 1, 2011

(86) PCT No.: PCT/EP2011/006049
§ 371 (c)(1),
(2), (4) Date: Jul. 22, 2013

(87) PCT Pub. No.: WO2012/076134
PCT Pub. Date: Jun. 14, 2012

(65) Prior Publication Data
US 2013/0302459 A1 Nov. 14, 2013

(30) Foreign Application Priority Data
Dec. 9, 2010 (DE) .......................... 10 2010 053 873

(51) Int. Cl.
*A61C 13/20* (2006.01)
*F27B 17/02* (2006.01)

(52) U.S. Cl.
CPC ............... *A61C 13/20* (2013.01); *F27B 17/025* (2013.01); *Y10S 425/003* (2013.01)

(58) Field of Classification Search
CPC .... A61C 13/20; A61C 13/081; F27B 17/025; B29C 43/36; B29C 39/38; B22D 27/02
USPC ........... 264/40.1, 16–19; 425/78, 3, DIG. 33, 425/150, 170, 171, 174, 174.6; 100/280–286
See application file for complete search history.

(56) References Cited

U.S. PATENT DOCUMENTS

| 2,228,916 | A | * | 1/1941 | Simons ........................... 419/18 |
| 3,069,742 | A | * | 12/1962 | Walchhuetter ................ 425/406 |
| 4,536,366 | A | * | 8/1985 | Inoue .............................. 419/11 |
| 6,303,059 | B1 | | 10/2001 | Foser et al. |
| 6,612,826 | B1 | * | 9/2003 | Bauer et al. ................... 425/135 |
| 7,325,433 | B2 | * | 2/2008 | Foser .............................. 264/16 |
| 2002/0102519 | A1 | * | 8/2002 | Baum et al. .................... 264/19 |
| 2010/0028477 | A1 | | 2/2010 | Ryu et al. |

FOREIGN PATENT DOCUMENTS

| DE | 3500267 A1 | 7/1986 |
| EP | 0438802 A1 | 7/1991 |
| JP | 8281405 A | 10/1996 |

OTHER PUBLICATIONS

International Search Report for Application PCT/EO2011/006049, Report completed Apr. 5, 2012, 3 pgs.

\* cited by examiner

*Primary Examiner* — Joseph S Del Sole
*Assistant Examiner* — Thukhanh Nguyen
(74) *Attorney, Agent, or Firm* — KPPB LLP

(57) ABSTRACT

The invention relates to a press furnace for a denture or partial denture, having a combustion chamber in which a press mold, in particular a muffle, having a press channel for the introduction of a ram can be positioned, and a drive for driving the ram, wherein, in order to improve the drive of the press furnace, the drive provided is an electromagnet, the magnetic armature or magnetic coil of which drives the ram.

9 Claims, 1 Drawing Sheet

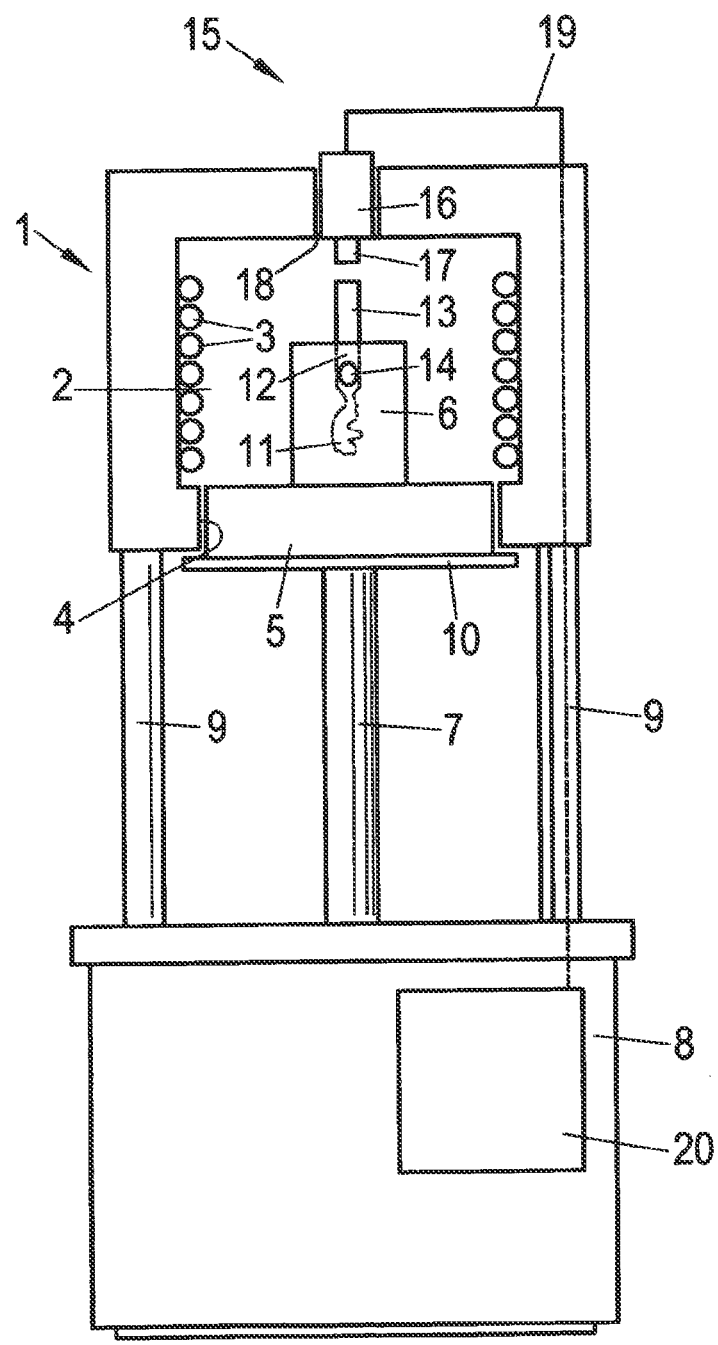

PRESS FURNACE FOR A DENTURE OR PARTIAL DENTURE

The present invention relates to a press furnace for a denture or a partial denture having a firing chamber in which a mold in particular a muffle, having a press passage for introducing a press plunger can be positioned and having a drive for driving the press plunger.

With such press furnaces, the starting material for the denture or partial denture is usually heated in the form of pellets in a so-called muffle and is pressed into shape. For this purpose, the muffle has a hollow space which was previously manufactured with the aid of a push mold and which corresponds to the shape of the denture or partial denture to be manufactured. The denture compound is pressed into the hollow space via a plunger and is held under pressure there for at least as long until the hollow space is completely filled.

It is the underlying object of the invention to provide a press furnace of the initially named kind having an improved drive.

This object is satisfied in that an electromagnet is used as the drive whose armature or coil drives the press plunger.

The use of an electromagnet as the drive has the advantage that the press furnace can have a very simple design. The space requirements are comparatively small and no pressure connection is required as with press furnaces having a pressure drive or a vacuum drive. A large force can also be exerted on the press plunger by means of an electromagnet.

The use of an alternating-current magnet is particularly preferred. It is characterized by a large linearity of the force-displacement characteristic of the moved armature with respect to the coil. A particularly high linearity is present with a plunger coil magnet in which the coil moves relative to the permanent magnet.

In accordance with a preferred embodiment of the invention, means are provided for measuring the power consumption of the electromagnet as well as means for determining the force exerted on the press plunger with reference to the power consumption. This allows a simple and good measurement of the force exerted by the press plunger onto the material to be pressed without additional devices being necessary here. The measured force can be used for controlling or regulating the press furnace, for example to adjust a predefined force or to recognize the end of the pressing process with reference to a force increase. The measured power consumption or the force determined therefrom can also be used to shorten a preset pressing time. This can also take place in a plurality of steps.

In accordance with a preferred embodiment of the invention, means are provided for measuring the pressure drop at the electromagnet or the current consumption of the electromagnet as well as means for determining the position of the plunger on the basis of the measured voltage or of the measured current consumption. The path covered by the press plunger can thereby be measured in a simple manner with high precision and without additional devices. The measured path can then in turn be used for controlling or regulating the press furnace, for example to regulate the penetration speed of the press plunger or to recognize an end of the pressing process.

The measured voltage drop or the current consumption of the electromagnet or the position of the plunger determined therefrom can be used to shorten a preset pressing time, likewise also again in a plurality of steps.

The firing chamber of the press furnace can furthermore be able to be evacuated or partly evacuated and/or can be fillable with inert gas. It is thereby possible to press a denture or a partial denture under a desired atmosphere.

An embodiment of the invention is represented in the drawing and will be described in the following. The only FIGURE shows FIG. 1 a partly sectioned side view of a press furnace in accordance with the invention.

The press furnace shown comprises a furnace housing 1 having a firing chamber 2 present therein and a heating coil 3 present in the firing chamber 2. The firing chamber 2 has an opening 4 at its lower side through which a carrier 5 for a muffle 6 can be moved in and out of the firing chamber 2. A lift 7 which engages at the lower side of the carrier 5 is provided for moving the carrier 5 in and out.

The lift 7 can be actuated by a drive, not shown here, present in a socket housing 8 arranged beneath the furnace housing 1. The socket housing 8 supports the furnace housing 1 via columns 9. A plate 10 is arranged at the lower side of the carrier 5 via which the firing chamber 2 can be closed gas-tight with a moved-in carrier 5.

The muffle 6 has a hollow space 11 whose shape corresponds to a desired denture or part denture and was previously manufactured in a known manner with the aid of a model. The hollow space 11 is connected to a passage 12 which opens at the upper side of the muffle 6. The passage 12 serves as a guide for a press plunger 13 and for receiving a pellet 14 of dental prosthetic material. A drive 15 for the press plunger 13 is provided above the muffle 6 and opposite the firing chamber opening 4. Said drive comprises an electromagnet 16 having a coil, not shown here, and an armature 17. The electromagnet is inserted into a cut-out 18 in the upper side of the furnace housing 1. The armature 17 is axially aligned with the press plunger 13 and is configured for driving the press plunger 13.

The electromagnet 16 is supplied with current for this purpose, which takes place via a feed line 19 which is, on the other hand, connected to an energy supply and control unit 20 in the socket housing 8 of the press furnace. On the supply of current to the electromagnet, 16, the armature 17 moves out of the electromagnet 16 and drives the press plunger 13 into the press passage 12 of the muffle 16.

A previously manufactured muffle 6 having a mold space 11, a press passage 12 and a pellet 14 of dental prosthetic material arranged therein is positioned on the carrier 5 of the press furnace moved out of the firing chamber 2 for manufacturing a denture or a partial denture. A press plunger 13 is inserted into the press passage 12 of the muffle 6. The carrier 5 with the muffle 6 is then moved via the lift 7 into the firing chamber 2, with the latter being sealed gas-tight by the plate 10.

To exert a specific pressing pressure on the press plunger 13, the electromagnet 16 now has current supplied to it via the line 19, after the firing chamber 2 has, when desired, been evacuated, partially evacuated and/or flooded with inert gas and after the pellet 4 has been sufficiently heated, such that the armature 17 exerts a desired pressure or a desired pressing force on the press plunger 13. This pressing force is transmitted from the press plunger 13 onto the dental prosthetic material 14. A desired pressing force distribution over time can then be realized via the control unit, 20. This can take place, for example, in that the power consumption of the electromagnet 16 is measured and the exerted pressing force is calculated from the power consumption. Another possibility is to determine the position of the armature 17, and thus of the press plunger 13, from the voltage drop at the electromagnet 16 or from its current consumption. The penetration path can be calculated via the position of the press plunger 13.

After the end of pressing, the firing chamber 2 is optionally ventilated. The firing chamber can then be opened by moving down the carrier 5 and the muffle 6 with the manufactured denture or partial denture can be removed.

REFERENCE NUMERAL LIST

1 firing chamber housing
2 firing chamber
3 heating device
4 lower opening of 1
5 carrier
6 muffle
7 lift
8 socket housing
9 column
10 plate
11 mold space
12 press passage
13 press plunger
14 pellet
15 drive
16 electromagnet
17 armature
18 cut-out
19 supply line
20 supply and control unit

The invention claimed is:

1. A press furnace for a denture or a partial denture comprising
   a firing chamber,
   a press mold having a press passage for introducing a press plunger, which press mold can be positioned in the firing chamber,
   an electromagnetic drive comprising at least an armature and a coil, wherein one of the armature and coil of the electromagnetic drive applies a pressing force to drive the press plunger into the press passage of the press mold, and
   a current supply in electrical communication with the electromagnetic drive for supplying a current thereto, wherein the pressing force is dependent on the current consumption of the electromagnetic drive.

2. The press furnace in accordance with claim 1, wherein the press mold is a muffle.

3. The press furnace in accordance with claim 1, wherein the electromagnet is configured as an alternating-current magnet.

4. The press furnace in accordance with claim 1, further comprising means for measuring a power consumption of the electromagnet as well as means for determining a force exerted on the press plunger with reference to the measured power consumption.

5. The press furnace in accordance with claim 1, further comprising means for measuring one of a voltage drop at the electromagnet and a current consumption of the electromagnet as well as means for determining the position of one of the armature and of the coil, and from this the position of the press plunger on the basis of a measured voltage or of the measured power consumption.

6. The press furnace in accordance with claim 1, wherein the firing chamber can be at least partly evacuated.

7. The press furnace in accordance with claim 1, wherein the firing chamber can be filled with inert gas.

8. The press furnace in accordance with claim 1, further comprising means by which a preset press time can be shortened in one or more steps in dependence on measured furnace parameters.

9. The press furnace in accordance with claim 8, wherein the measured furnace parameters comprise a member of the group consisting of the power consumption of the electromagnet, the current consumption of the electromagnet and the voltage drop at the electromagnet.

* * * * *